United States Patent [19]  [11] 4,154,819
Stephan  [45] May 15, 1979

[54] PREPARATION OF A GAMMA-GLOBULIN SOLUTION SUITABLE FOR INTRAVENOUS ADMINISTRATION USING DIKETENE

[75] Inventor: Wolfgang Stephan, Dreieichenhain, Fed. Rep. of Germany

[73] Assignee: Biotest-Serum-Institut GmbH, Frankfurt, Fed. Rep. of Germany

[21] Appl. No.: 721,130

[22] Filed: Sep. 7, 1976

[30] Foreign Application Priority Data

Sep. 6, 1975 [DE] Fed. Rep. of Germany ....... 2539800
Apr. 3, 1976 [DE] Fed. Rep. of Germany ....... 2614503

[51] Int. Cl.² .......................... A23J 1/06; C07G 7/00
[52] U.S. Cl. .................................... 424/101; 424/177; 260/112 B
[58] Field of Search .................... 260/112 B; 424/177, 424/101

[56] References Cited

U.S. PATENT DOCUMENTS 3,916,026  10/1975  Stephan ................................ 424/177

OTHER PUBLICATIONS

Chem. Abstracts, vol. 75, 1971, 17954k, Stephan.
Noller, 2nd Edition Chemistry of Organic Compounds, 1957, pp. 762, 782 and 824–825.
Chem. Abstracts, vol. 84, 1976, 132339m, Heremans et al., effective date 2/5/76.

*Primary Examiner*—Howard E. Schain
*Attorney, Agent, or Firm*—Sprung, Felfe, Horn, Lynch & Kramer

[57] ABSTRACT

In the preparation of a gamma-globulin solution suitable for the intravenous application by reaction of a solution of standard gamma-globulin with a reagent to combine with the anticomplementary material contained therein and separating the solution from the solids, the improvement which comprises employing as said reagent at least one member selected from the group consisting of acetimido ethyl ester hydrochloride, diketene, propanesultone and formimido ethyl ester hydrochloride.

2 Claims, No Drawings

PREPARATION OF A GAMMA-GLOBULIN SOLUTION SUITABLE FOR INTRAVENOUS ADMINISTRATION USING DIKETENE

The present invention relates to a process for the preparation of a gamma-globulin solution suitable for intravenous administration.

My U.S. Pat. No. 3,916,026 describes a process for the production of a gamma-globulin solution suitable for intravenous application, which involves reacting a solution of standard gamma-globulin at room temperature and a pH value of about 8.0 with about 0.043 ml of β-propiolactone per gram of protein, allowing it to stand for about one hour, then allowing it to stand at about 37° C. for about 3.5 hours at a pH value of about 8.0, followed by dialysis and sterile filtration.

Surprisingly, it has now been discovered that, instead of β-priopiolactone, this process can be effected with other compounds which remove the anticomplementary activity of the staring material, so as still to obtain a gamma-globulin suitable for intravenous application. According to the invention, with a solution of standard gamma-globulin, per gram of protein, there is reacted approximately 0.055 g of acetimido ethyl ester hydrochloride, or 0.022 g of diketene, or 0.05 g of formimido ethyl ester hydrochloride or 0.077 g of propanesultone at a pH of about 9.0. Thereafter the pH is brought to about 7 to 7.5 and the solution purified as by dialysis and sterile filtrations.

With the formimid and acetimid ethyl ester hydrochlorides and diketene the temperature of the reaction is advantageously about 5° C. whereas with propanesultone it is advantageously about 37° C.

The reagents used according to the invention display special advantages vis-a-vis beta-propiolactone. Thus, the acetimido acid ethyl ester hydrochloride has the advantage of greater reactivity, whereby it is possible to work under milder reaction conditions. Moreover, this reagent is more easily producible, whereas, as is known, beta-propiolactone can only be produced under very difficult conditions. Diketene also reacts faster than β-propiolactone and can therefore be used under reaction conditions which protect the treated proteins. Propanesultone during the reaction according to the invention with the protein forms a sulfonamide-like structure which per se has antibacterial activity. The effect desired according to the instant invention is therefore assisted and supported by this reagent. Of the new reagents formimido ethyl ester hydrochloride has the advantage that it has the lowest molecular weight and therefore during its use the change effected during the reaction with protein is especially small; therefore during continuous use of the gamma-globulin solution an especially good tolerance results.

The invention is further described in the following illustrative examples wherein all parts are by weight unless otherwise expressed.

EXAMPLE 1

100 ml of standard gamma-globulin solution with a protein content of about 5% are reacted at 5° C. with 0.055 g of acetimide ethyl ester hydrochloride per gram of protein at a pH value of 9.0 for two hours. Then the pH is adjusted to 7.0 by addition of NaOH, the solution is dialyzed against physiological sodium chloride solution and sterile filtered. The immunoglobulins in the resulting solution have a relatively long shelf life and are suited for intravenous administration wherever gamma-globulin administration is indicated.

Substantially similar results are obtained if the dialysis step is replaced by conventional fractionation.

EXAMPLE 2

100 ml of standard gamma-globulin solution with a protein content of about 5% are reacted with 0.022 g of diketene per gram of protein at a pH of 9.0 and 5° C. for two hours. Then the pH value is adjusted to 7.0, the solution is dialyzed against physiological sodium chloride and sterile filtered or the dialysis is replaced by conventional fractionation. A product similar in properties to that of Example 1 is obtained.

EXAMPLE 3

100 ml of standard gamma-globulin solution with a protein content of about 5% are reacted with 0.077 g of propanesultone per gram of protein at a pH of 9.0 and 37° C. for four hours. Then the pH value is adjusted to 7.0, the solution dialyzed against physiological sodium chloride and sterile filtered or the dialysis is replaced by conventional fractionation.

EXAMPLE 4

100 ml of standard gamma-globulin solution with a protein content of about 5% are reacted with 0.05 g of formimido ethyl ester hydrochloride per gram of protein at a pH of 9.0 and 5° C. After two hours of stirring the pH is brought to 7.5 the solution is dialyzed against physiological NaCl and sterile filtered. Concentration of the resulting solution is achieved by ultra-filtration or by conventional fractionation such as with Rivanol ammonium sulfate or alcohol.

While the invention has been illustrated with particular amounts of complement-binding reagents, greater or lesser amounts can be used. Lesser amounts do not remove all the complement-binding material while larger amounts may require removal of excess reagent. In place of formimido or acetimido ethyl ester hydrochlorides, other lower alkyl esters can be employed in equivalent amounts and/or the free esters or salts with other acids can be employed, e.g. the hydrobromide or sulfate.

The ultimate purification techniques can also be varied considerably, e.g. fractional precipitations, evaporation to dryness followed by water extraction of the active material, and the like.

It will be appreciated that the instant specification and examples are set forth by way of illustration and not limitation, and that various modifications and changes may be made without departing from the spirit and scope of the present invention.

What is claimed is:

1. In the preparation of a gamma-globulin solution suitable for the intravenous application by reaction of a solution of standard gamma-globulin with a reagent to combine with the anticomplementary material contained therein and separating the solution from the solids, the improvement which comprises employing as said reagent diketene, effecting the reaction at about 5° C. and a pH of about 9, thereafter adjusting the pH to about 7 to 7.5, and separating the solution from the solids by dialysis or fractionation followed by sterile filtration.

2. A process according to claim 1, wherein the diketene is employed in about 0.022 g per g of protein in the gamma-globulin solution.

* * * * *